(12) United States Patent
Yamaguchi et al.

(10) Patent No.: US 12,702,815 B2
(45) Date of Patent: Aug. 11, 2026

(54) EXTRACORPOREAL CIRCULATION CIRCUIT

(71) Applicant: NIPRO CORPORATION, Osaka (JP)

(72) Inventors: Takeshi Yamaguchi, Osaka (JP); Sachiko Ishida, Osaka (JP)

(73) Assignee: NIPRO CORPORATION, Osaka (JP)

( * ) Notice: Subject to any disclaimer, the term of this patent is extended or adjusted under 35 U.S.C. 154(b) by 356 days.

(21) Appl. No.: 18/275,270

(22) PCT Filed: Feb. 4, 2022

(86) PCT No.: PCT/JP2022/004422

§ 371 (c)(1),
(2) Date: Aug. 1, 2023

(87) PCT Pub. No.: WO2022/168938

PCT Pub. Date: Aug. 11, 2022

(65) Prior Publication Data

US 2024/0299727 A1 Sep. 12, 2024

(30) Foreign Application Priority Data

Feb. 4, 2021 (JP) ................................ 2021-016772

(51) Int. Cl.
*A61M 60/113* (2021.01)
*A61M 1/36* (2006.01)
(Continued)

(52) U.S. Cl.
CPC .......... *A61M 60/113* (2021.01); *A61M 1/367* (2013.01); *A61M 60/279* (2021.01); *A61M 60/37* (2021.01); *F04B 43/1253* (2013.01)

(58) Field of Classification Search
CPC ............ F04B 43/1253; A61M 60/279; A61M 60/113; A61M 60/37; A61M 1/14; A61M 1/3621
See application file for complete search history.

(56) References Cited

U.S. PATENT DOCUMENTS 4,496,295 A 1/1985 King
2012/0150123 A1* 6/2012 Lawrence ............ A61M 5/427 206/370

(Continued)

FOREIGN PATENT DOCUMENTS

| | | | |
|---|---|---|---|
| EP | 2397695 | A1 | 12/2012 |
| JP | 2010-190062 | A | 9/2010 |
| WO | 2019/065480 | A1 | 4/2019 |

OTHER PUBLICATIONS

Jason Schwartz, Design Guidelines For All Stages of Injection Molding; https://revpart.com/design-guidelines-stages-injection-molding/, accessed Sep. 2, 2025, Published Oct. 13, 2016, captured by Wayback Machine Mar. 12, 2017 (Year: 2016).*

(Continued)

*Primary Examiner* — Ariana Zimbouski
(74) *Attorney, Agent, or Firm* — Renner, Otto, Boisselle & Sklar, LLP

(57) ABSTRACT

An extracorporeal circuit includes a tube holder holding a pump tube and line tubes. The tube holder has first and second tube holding portions holding the pump tube in a loop shape and holding the line tubes and a fixing plate coupling the first tube holding portion and the second tube holding portion to each other. The fixing plate is configured such that a line-tube-side end thereof is inclined to a pump tube side from a second tube holding portion side toward a first tube holding portion side.

11 Claims, 11 Drawing Sheets

(51) Int. Cl.

| | |
|---|---|
| ***A61M 60/279*** | (2021.01) |
| ***A61M 60/37*** | (2021.01) |
| ***F04B 43/12*** | (2006.01) |

(56) References Cited

U.S. PATENT DOCUMENTS

| | | | | |
|---|---|---|---|---|
| 2014/0012176 | A1 | 1/2014 | Schaefer et al. | |
| 2015/0018799 | A1* | 1/2015 | Lewis | A61M 39/08<br>604/533 |
| 2020/0230307 | A1 | 7/2020 | Sonoda et al. | |
| 2020/0368419 | A1* | 11/2020 | Engeln | A61M 1/1654 |

OTHER PUBLICATIONS

Extended European Search Report dated Jun. 4, 2024 in corresponding European Patent Application No. 22749809.4.
European Office Action dated Feb. 7, 2025 in corresponding European Patent Application No. 22749809.4.
International Search Report for corresponding Application No. PCT/JP2022/004422, mailed Apr. 5, 2022.

* cited by examiner

EXTRACORPOREAL CIRCULATION CIRCUIT

TECHNICAL FIELD

The present disclosure relates to an extracorporeal circuit, and particularly relates to an extracorporeal circuit having a holder attached to a dialysis machine.

BACKGROUND ART

As, e.g., a blood pump of a dialysis machine used for dialysis treatment, a tube pump that delivers liquid such as blood by squeezing a pump tube by a rotating rotor has been used. In the case of the dialysis machine, a blood circuit including a pump tube needs to be replaced in every dialysis treatment. A plurality of tubes other than the pump tube is connected to the blood circuit, and these tubes need to be correctly attached to correct positions without, e.g., twist. Particularly, great force is on a pump tube portion, and for this reason, if the tubes are not correctly attached, there is a probability that liquid cannot be delivered or the tube is damaged.

In order to easily and correctly attach the pump tube, study has been conducted on a method in which a holder to which a pump tube portion of a blood circuit is fixed is attached to a pump. The holder is configured such that two holding portions holding both end portions of the pump tube are fixed to a fixing plate, and the pump tube in a loop shape is automatically aligned by attaching the plate to a housing of the pump (see, e.g., Patent Document 1). After having attached the plate to the pump, a user assembles a tube on a line side opposite to the pump with a dialysis machine, thereby attaching the blood circuit to the dialysis machine.

CITATION LIST

Patent Document

PATENT DOCUMENT 1: Japanese Unexamined Patent Publication No. 2010-190062

SUMMARY OF THE INVENTION

Technical Problem

The conventional blood circuit is assembled with the dialyzer such that the line-side tube extends in the right-left direction, thereby preventing a situation where the line-side tube is forcibly bent and kink of the tube occurs in the vicinity of the plate. However, in this case, an entire tube length is long, and the dialyzer is increased in size.

Further, due to a problem in, e.g., layout at an installation location, there are a dialyzer configured such that a pump tube is set to a pump from the left side and a dialyzer configured such that a pump tube is set to a pump from the right side. The conventional holder is in an asymmetric shape, and one for a device for left layout and one for a device for right layout need to be separately prepared.

Further, the fixing plate is a thin member, and for this reason, distortion is easily caused and there is a probability that a defect is caused upon attachment to the pump particularly in a case where the center line of the fixing plate is shifted from the up-down direction. In addition, the fixing plate is formed as a member separated from the tube and is assembled after molding, and for this reason, there is a problem that a manufacturing cost increases. Moreover, the fixing plate whose center line is shifted from the up-down direction is out of balance upon molding, and for this reason, releasability from a mold is poor.

Further, since the plate is used, an error in attachment of the tube is less likely to occur, but an operation of engaging the pump tube to the rotor after the plate has been attached to the housing is not taken into consideration. Particularly, in the case of the device configured such that the pump tube is automatically engaged with the rotor, there is a problem that the pump tube attached to the plate interferes with engagement with the rotor or is deformed and damaged.

Further, there has been a demand for easy detachment of the plate from the housing after use. However, even if engagement force between the plate and the housing is decreased in order to easily detach the plate, the plate is easily accidentally dropped. In addition, there is a problem that due to a complicated detachment mechanism on a device side, the device is increased in size.

Further, in a case where the pump tube is fixed to the fixing plate, the pump tube is bent in a loop shape with a small curvature radius. For this reason, there is a problem that stress is on the pump tube due to a long storage period after the extracorporeal circuit has been manufactured and the tube is deteriorated and bent. If the pump tube is shortened due to a size decrease in the device, the curvature radius decreases, and accordingly, the kink leading to bending of the tube is more easily caused.

An object of the present disclosure is to solve at least one of these problems.

Solution to the Problem

A first aspect of an extracorporeal circuit of the present disclosure is an extracorporeal circuit assembled with a dialysis machine having a pump portion provided on a side surface of a housing, the extracorporeal circuit including a pump tube assembled with a rotor of the pump portion, a line tube, and a tube holder holding the pump tube and the line tube. The tube holder has first and second tube holding portions holding the pump tube in a loop shape and holding the line tube and a fixing plate coupling the first tube holding portion and the second tube holding portion to each other, and the fixing plate is configured such that a line-tube-side end thereof is inclined to a pump tube side from the second tube holding portion toward the first tube holding portion.

According to the first aspect of the extracorporeal circuit, the fixing plate of the tube holder is configured such that the line-tube-side end is inclined. Thus, even in the case of being assembled with a dialysis machine such that a line tube is drawn out downwardly from a pump in order not to increase an entire length, kink is less likely to occur in the vicinity of the fixing plate.

A second aspect of the extracorporeal circuit of the present disclosure is an extracorporeal circuit having a tube holder assembled, in the right-left direction of a pump portion provided on a side surface of a housing of a dialysis machine, with the dialysis machine having the pump portion and a line assembly portion provided below the pump portion, the extracorporeal circuit including a pump tube assembled with a rotor of the pump portion, a line tube having a line assembly target portion assembled with the line assembly portion, and a tube holder holding the pump tube and the line tube. The tube holder has first and second tube holding portions holding the pump tube in a loop shape and holding the line tube and a fixing plate coupling the first tube holding portion and the second tube holding portion to each other, a line-tube-side end portion of the first tube holding portion is positioned closer to a pump tube side than a line-tube-side end portion of the second tube holding portion is to the pump tube side, and a pump-tube-side end portion of the second tube holding portion is positioned closer to a line tube side than a pump-tube-side end portion of the first tube holding portion is to the line tube side.

According to the second aspect of the extracorporeal circuit, the line-tube-side end portion of the first tube holding portion is positioned closer to the pump tube side than the line-tube-side end portion of the second tube holding portion is to the pump tube side, and the pump-tube-side end portion of the second tube holding portion is positioned closer to the line tube side than the pump-tube-side end portion of the first tube holding portion is to the line tube side. Thus, when the assembly target portion of the line tube is assembled with the line assembly portion provided below the pump portion, the curvature radius of the line tube can be increased, and therefore, the kink is less likely to occur in the vicinity of the fixing plate.

In the second aspect of the extracorporeal circuit, the line tube may have a movement restrictor that restricts downward movement of the line tube. With this configuration, dropping of the pump tube can be prevented even in the case of pulling the line tube downwardly.

A third aspect of the extracorporeal circuit of the present disclosure is an extracorporeal circuit assemblable with any of a first dialysis machine configured such that a rotor of a pump portion provided on a side surface of a housing and an attachment target portion are in a first positional relationship and a second dialysis machine configured such that a positional relationship of an attachment target portion with a rotor of a pump portion is a second positional relationship opposite to the first positional relationship, the extracorporeal circuit including a pump tube assembled with the rotor of the pump portion, a line tube, and a tube holder holding the pump tube and the line tube. The tube holder has first and second tube holding portions holding the pump tube in a loop shape and holding the line tube, a fixing plate coupling the first tube holding portion and the second tube holding portion to each other, a first attachment portion for attachment to the first dialysis machine in a state in which a first surface of the fixing plate faces a first dialysis machine side, and a second attachment portion for attachment to the second dialysis machine in a state in which a second surface opposite to the first surface faces the second dialysis machine.

According to the third aspect of the extracorporeal circuit, the extracorporeal circuit can be assembled with any of the first dialysis machine and the second dialysis machine by turning back.

A fourth aspect of the extracorporeal circuit of the present disclosure is an extracorporeal circuit assembled with a dialysis machine having a pump portion on a side surface of a housing, the extracorporeal circuit including a pump tube assembled with a rotor of the pump portion, a line tube, and a tube holder holding the pump tube and the line tube. The tube holder has first and second tube holding portions holding the pump tube in a loop shape and holding the line tube and a fixing plate coupling the first tube holding portion and the second tube holding portion to each other. The fixing plate has an end portion inclined from a first tube holding portion side toward a second tube holding portion side, and has a less-bendable portion provided with a rib and an easily-bendable portion provided between the less-bendable portion and at least one of the first tube holding portion or the second tube holding portion and formed more bendable than the less-bendable portion.

According to the fourth aspect of the extracorporeal circuit, the fixing plate has the easily-bendable portion provided between the less-bendable portion and the at least one of the first tube holding portion or the second tube holding portion and formed more bendable than the less-bendable portion. With this configuration, the tube holding portion side can be deformed to some extent while occurrence of distortion of the fixing plate at the center portion is reduced, and therefore, the tube holder can be easily assembled with the dialysis machine.

A fifth aspect of the extracorporeal circuit of the present disclosure is an extracorporeal circuit assembled with a dialysis machine having a pump portion on a side surface of a housing, the extracorporeal circuit including a pump tube assembled with a rotor of the pump portion, a line tube, and a tube holder holding the pump tube and the line tube. The tube holder has first and second tube holding portions holding the pump tube in a loop shape and holding the line tube and a fixing plate coupling the first tube holding portion and the second tube holding portion to each other, and has a parting line between a pump-tube-side mold portion and a line-tube-side mold portion. The fixing plate has an angle changing portion on a line tube side with respect to the parting line, and the angle changing portion has such a tapered surface that a thickness thereof gradually decreases toward the line tube side.

According to the fifth aspect of the extracorporeal circuit, the fixing plate has the angle changing portion on the line tube side with respect to the parting line, and the angle changing portion has such a tapered surface that the thickness thereof gradually decreases toward the line tube side. Thus, when the tube holder is molded using a die separatable into a pump-tube-side portion and a line-tube-side portion, a molded article does not remain in the line-tube-side mold. Thus, productivity can be greatly improved.

A sixth aspect of the extracorporeal circuit of the present disclosure is an extracorporeal circuit assembled with a dialysis machine having a pump portion on a side surface of a housing, the extracorporeal circuit including a pump tube assembled with a rotor of the pump portion, a line tube, and a tube holder holding the pump tube and the line tube. The tube holder has first and second tube holding portions holding the pump tube in a loop shape and holding the line tube and a fixing plate coupling the first tube holding portion and the second tube holding portion to each other, and has a parting line between a pump-tube-side mold portion and a line-tube-side mold portion. The parting line has an inclined line extending in a direction inclined with respect to axial directions of the first tube holding portion and the second tube holding portion.

According to the sixth aspect of the extracorporeal circuit, when the tube holder is molded using the die separatable into the pump-tube-side portion and the line-tube-side portion, the depth of a cavity provided in the pump-tube-side mold can be substantially the same between the first tube holding portion and the second tube holding portion, and mold balance can be improved. Thus, releasability can be improved.

According to a seventh aspect of the extracorporeal circuit of the present disclosure is an extracorporeal circuit assembled with a dialyzer having a pump portion on a side surface of a housing, the extracorporeal circuit including a pump tube assembled with a rotor of the pump portion, a line tube, and a tube holder holding the pump tube and the line tube and detachably fixed to a housing of a pump portion. The tube holder has first and second tube holding portions, a fixing plate coupling the first tube holding portion and the second tube holding portion to each other, a first attachment portion formed so as to protrude to a side opposite to the second tube holding portion from the first tube holding portion, and a second attachment portion formed so as to protrude to a side opposite to the first tube holding portion from the second tube holding portion. The line tube is attached to a back side of the first tube holding portion and the second tube holding portion, and the pump tube is attached to a front side in a loop shape such that blood is delivered from the first tube holding portion to the second tube holding portion. The first attachment portion is turnably attached to a first attachment target portion formed at the housing. The second attachment portion is attachable to a second attachment target portion formed at the housing by turning about the first attachment portion. A front end of the first attachment portion is positioned on the front side with respect to a front end of the second attachment portion.

According to the seventh aspect of the extracorporeal circuit, the front end of the turnable first attachment portion formed so as to protrude from the first tube holding portion is positioned on the front side with respect to the front end of the second attachment portion formed so as to protrude from the second tube holding portion and provided attachable to the second attachment target portion by turning about the first attachment portion. With this configuration, the first attachment portion can be arranged near the rotor of the pump portion, and therefore, the pump tube can be easily automatically attached to the rotor and the second attachment portion can be detached from the rotor. Consequently, curvature caused upon attachment of the pump tube to the rotor can be reduced, and damage of the pump tube is less likely to occur.

In the seventh aspect of the extracorporeal circuit, the second tube holding portion may function as a sensor driver that drives a tube holder attachment sensor provided at the housing when the second attachment portion is attached to the second attachment target portion. The second tube holding portion is a portion having a great position displacement between a state of the second attachment portion and the second attachment target portion engaging with each other and a state of the second attachment portion and the second attachment target portion disengaging from each other, and therefore, engagement and disengagement between the second attachment portion and the second attachment target portion can be easily detected.

An eighth aspect of the extracorporeal circuit of the present disclosure is an extracorporeal circuit assembled with a dialysis machine having a pump portion on a side surface of a housing, the extracorporeal circuit including a pump tube assembled with a rotor of the pump portion, a line tube, and a tube holder holding the pump tube and the line tube and detachably fixed to a housing of the pump portion. The tube holder has first and second tube holding portions holding the pump tube in a loop shape and holding the line tube and a fixing plate coupling the first tube holding portion and the second tube holding portion to each other. The fixing plate has a raised portion protruding from a center portion in a thickness direction, and the tube holder is released from the housing by pushing the raised portion by a pushing pin formed on the pump portion.

The fixing plate is bent by pushing the center portion of the fixing plate, and therefore, the tube holder can be easily detached from the housing. Moreover, by pushing the center portion of the fixing plate, the displacement of the pushed tube holder is greater as compared to the case of pushing an end portion of the fixing plate on the second tube holding portion side, and therefore, detachment is facilitated.

A ninth aspect of the extracorporeal circuit of the present disclosure is an extracorporeal circuit assembled with a dialysis machine having a pump portion, the extracorporeal circuit including a pump tube assembled with a rotor of the pump portion, a line tube, and a tube holder holding the pump tube and the line tube. The tube holder has first and second tube holding portions holding the pump tube in a loop shape and holding the line tube and a fixing plate coupling the first tube holding portion and the second tube holding portion to each other, and the pump tube is held in a twisted state between the first tube holding portion and the second tube holding portion.

Since the pump tube is held in the twisted state between the first tube holding portion and the second tube holding portion, the direction of residual stress in a direction of bending the pump tube can be shifted. Thus, even in the case of storing the extracorporeal circuit for a long period of time, bending of the pump tube is less likely to occur.

A tenth aspect of the extracorporeal circuit of the present disclosure is an extracorporeal circuit assembled with a dialysis machine having a pump portion, the extracorporeal circuit including a pump tube assembled with a rotor of the pump portion, a plurality of line tubes, and a tube holder holding the pump tube to form a loop. The pump tube is stored in a state in which both sides thereof with respect to a loop inflection position are bundled with at least some of the plurality of line tubes.

Since the pump tube is stored in a state in which both sides thereof with respect to the loop inflection position are bundled with the at least some of the plurality of line tubes, residual stress in a direction of bending the pump tube can be dispersed and relieved during storage. Thus, even in the case of storing the extracorporeal circuit for a long period of time, bending of the pump tube is less likely to occur.

Advantages of the Invention

According to the extracorporeal circuit of the present disclosure, at least one of various problems due to compactification of the dialysis machine and programs such as occurrence of failure in assembly with the dialysis machine and degradation of productivity can be solved.

DESCRIPTION OF EMBODIMENTS

As shown in FIGS. 1 to 5, an extracorporeal circuit according to one embodiment has a pump tube 201, an inlet-side line tube 202A and an outlet-side line tube 202B, and a tube holder 100 for a pump. The tube holder 100 can be detachably attached to a housing of the pump.

Figure 1:
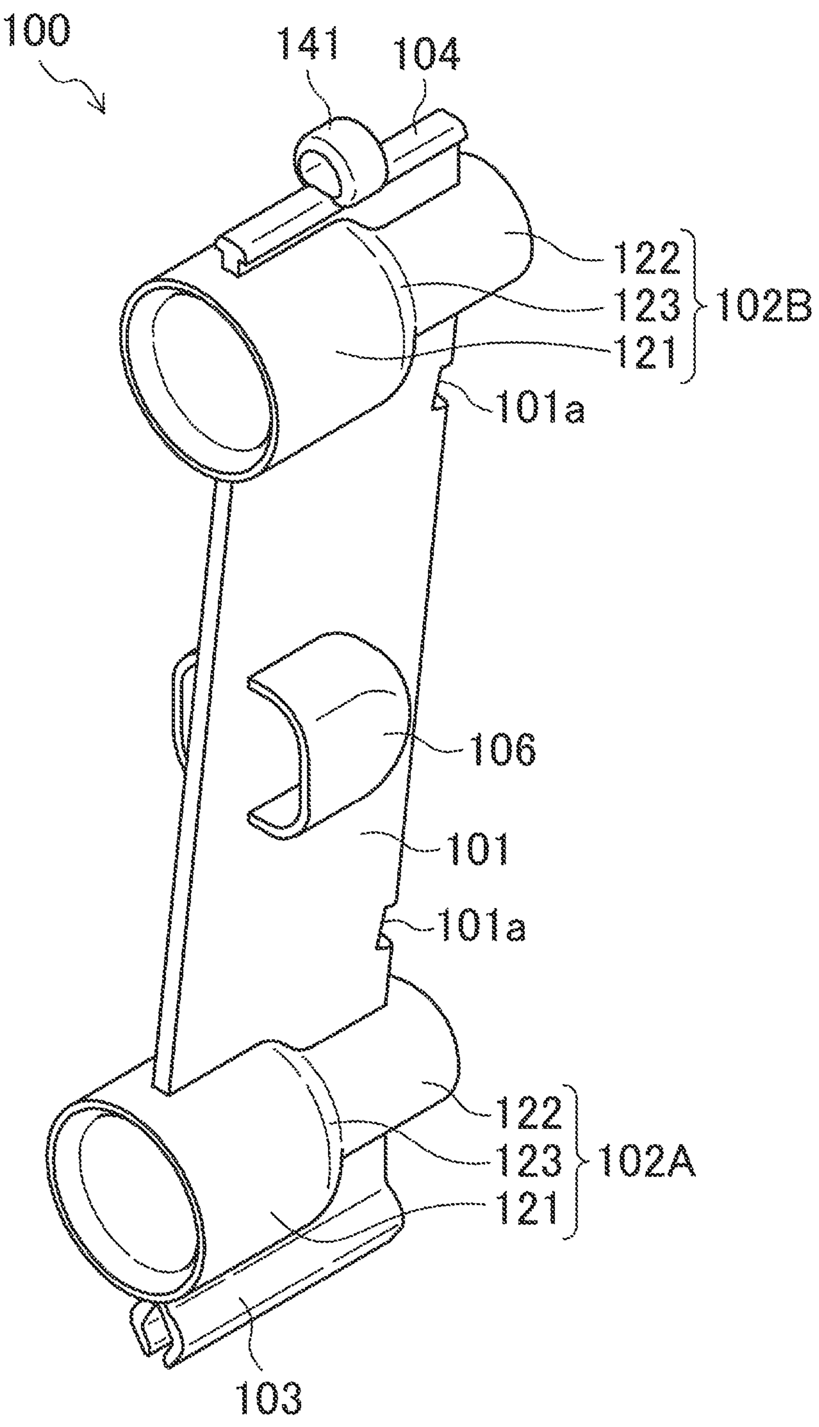
FIG. 1 is a perspective view showing a pump tube holder according to one embodiment.
Figure 2:
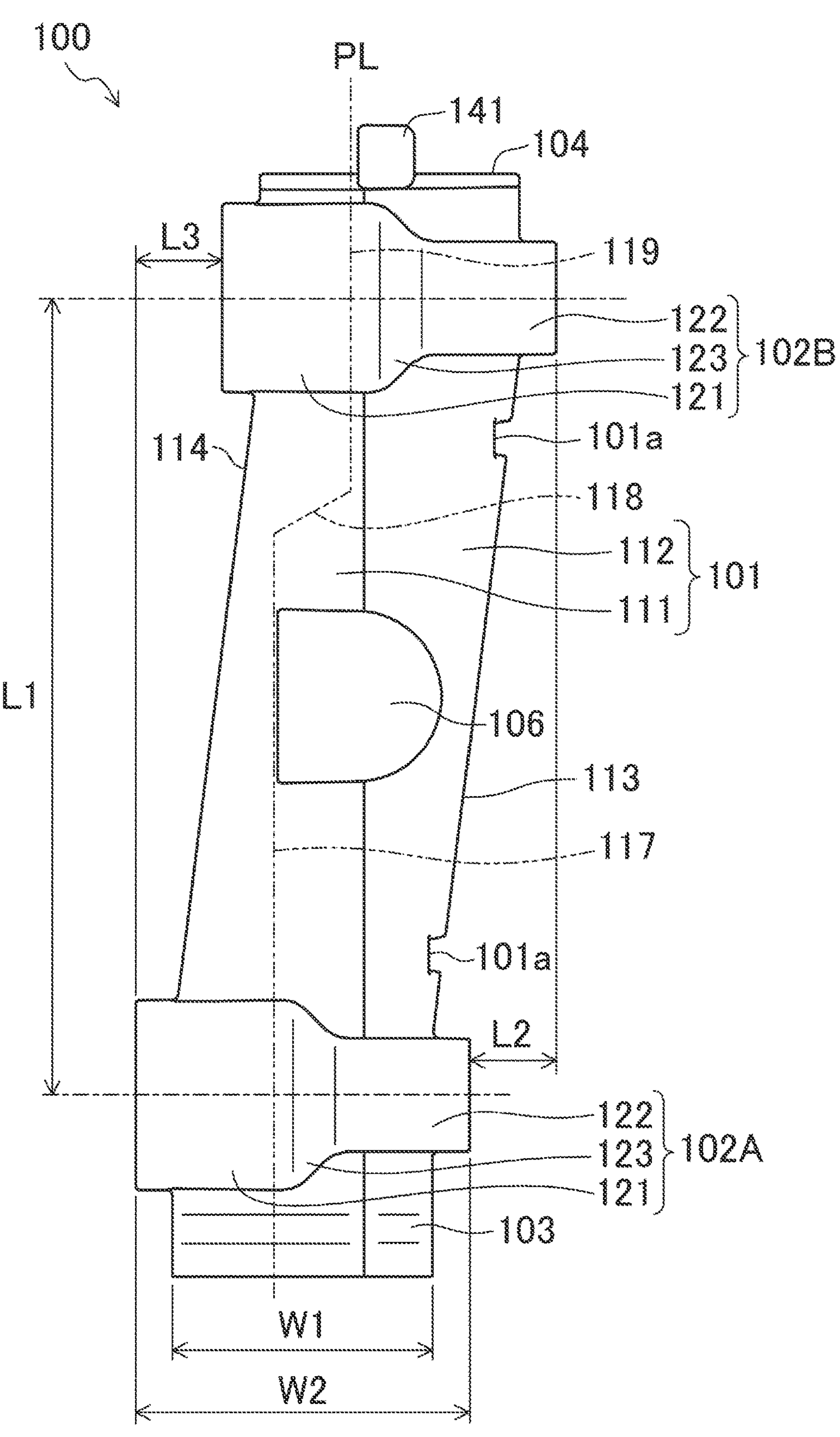
FIG. 2 is a plan view showing the pump tube holder according to one embodiment.
Figure 3:
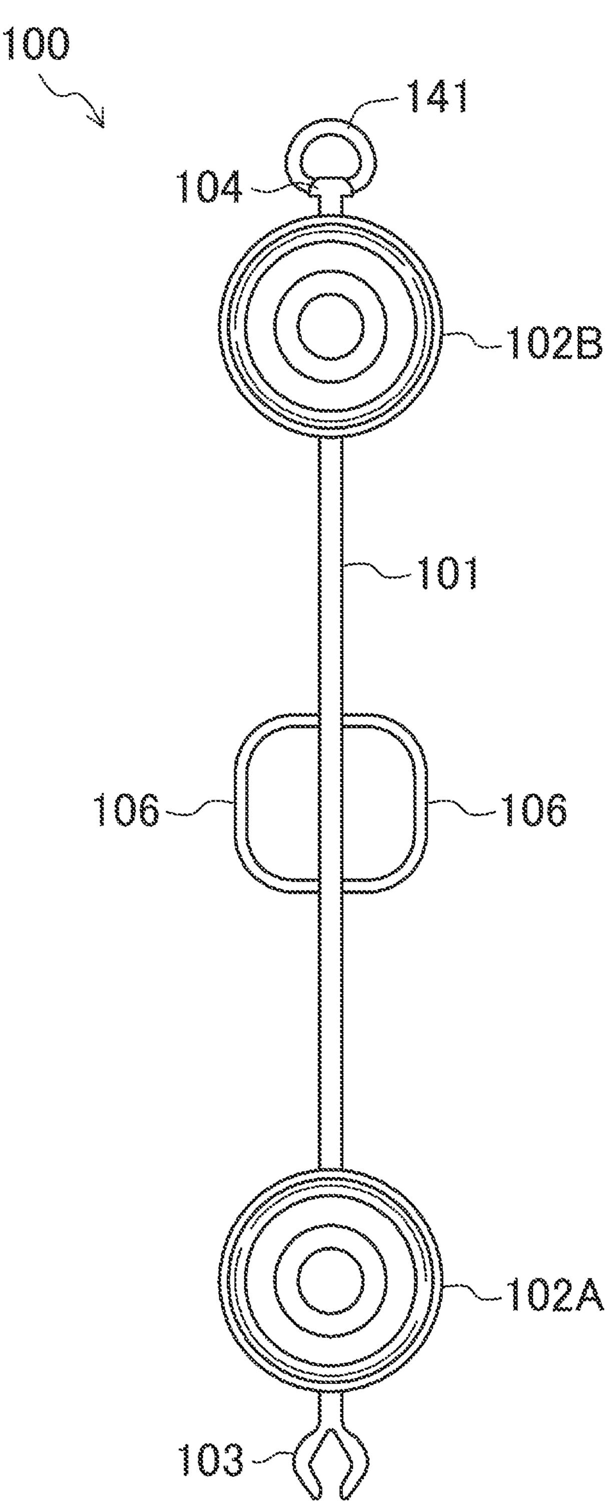
FIG. 3 is a front view showing the pump tube holder according to one embodiment.

As shown in FIGS. 1 to 3, the tube holder 100 according to one embodiment includes a plate-shaped fixing plate 101 and tubular first tube holding portion 102A and second tube holding portion 102B each fixed to both end portions of the fixing plate 101 and provided such that the axial directions thereof are parallel with each other.

The first tube holding portion 102A and the second tube holding portion 102B are in a tubular shape and has a large-diameter pump tube connection portion 121 and a line tube connection portion 122 having a smaller diameter than that of the pump tube connection portion 121. The pump tube connection portion 121 and the line tube connection portion 122 are connected to each other through a tapered portion 123 whose diameter changes.

In description below, a side on which the pump tube is connected will be referred to as a front side, a side on which the line tube is connected will be referred to as a back side, a first tube holding portion 102A side will be referred to as a lower side, and a second tube holding portion 102B side will be referred to as an upper side. Thus, when the tube holder 100 is attached to the housing of the pump, a rotor side is the front side, and the opposite side thereof is the back side.

Figure 4:
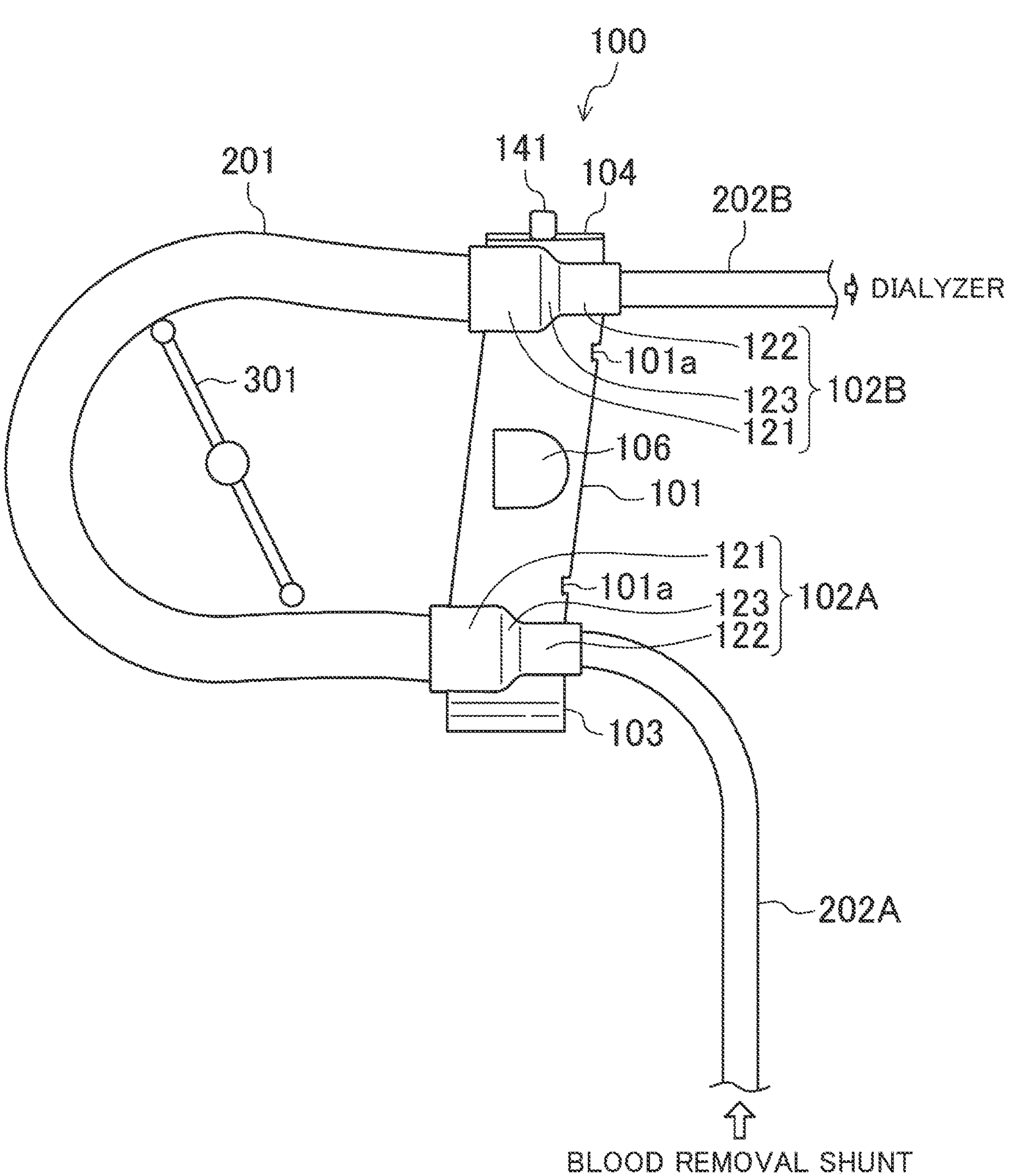
FIG. 4 is a view showing a use example of a blood circuit using the pump tube holder according to one embodiment.

As shown in FIG. 4, the pump tube 201 squeezed by a rotor 301 of the pump to deliver liquid is connected to the pump tube connection portions 121. The pump tube 201 is connected, at one end portion thereof, to the pump tube connection portion 121 of the first tube holding portion 102A, and at the other end portion, is connected to the pump tube connection portion 121 of the second tube holding portion 102B. Thus, the pump tube 201 forms a U-shaped loop. The inlet-side line tube 202A for guiding blood from a blood removal shunt to the pump is connected to the line tube connection portion 122 of the first tube holding portion 102A. The outlet-side line tube 202B for guiding blood delivered out of the pump to a dialyzer is connected to the line tube connection portion 122 of the second tube holding portion 102B.

Figure 5:
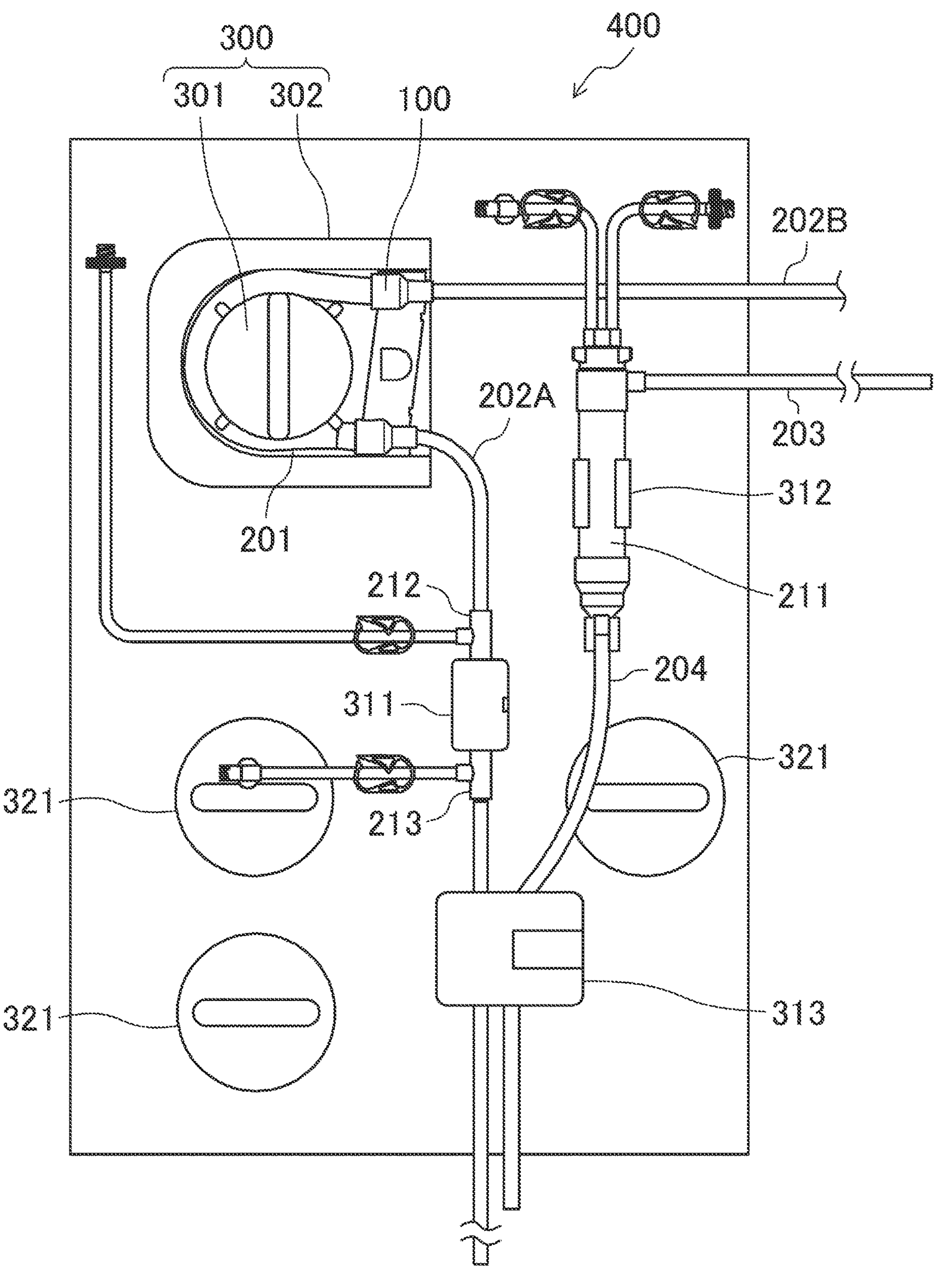
FIG. 5 is a view showing an example where the pump tube holder according to one embodiment is attached to a dialysis machine.

The tube holder 100 of the present embodiment can be attached to a pump 300 of a dialysis machine 400 as shown in FIG. 5. The pump 300 is arranged on a side surface of a housing of the dialysis machine 400 such that a direction of drawing in the pump tube 201 and a direction of drawing out the pump tube 201 are the horizontal direction. The inlet-side line tube 202A connected to the blood removal shunt of a patient is bent in the middle, and is drawn out downwardly from the dialysis machine 400. On the other hand, the outlet-side line tube 202B connected to the dialyzer is drawn out substantially in the horizontal direction.

A component sensor 311 that analyzes a component of blood flowing in the line, a liquid level sensor 312 that detects a liquid level in a drip chamber 211, a bubble sensor 313 that detects air bubbles in the line, etc. are arranged at the periphery of the pump 300 of the dialysis machine 400. Further, a plurality of ports 321 for supplying and discharging, e.g., dialysate is arranged. By operation of the pump 300, blood is extracted from the patient through the inlet-side line tube 202A, and is delivered to the dialyzer through the outlet-side line tube 202B. The blood purified by the dialyzer is delivered to the blood-return-side drip chamber 211 through a blood-return-side line tube 203, and air bubbles are removed therefrom. Then, the blood is returned to the patient's body through a line tube 204.

A line assembly portion to be assembled with an assembly target portion of the inlet-side line tube 202A is provided below the pump 300. Thus, the inlet-side line tube 202A is drawn out downwardly from the pump 300. In the present embodiment, the component sensor 311 functions as the line assembly portion. The component sensor 311 holds the inlet-side line tube 202A such that the inlet-side line tube 202A passes through a housing of the component sensor 311. Note that the line assembly portion is only required to be assembled with and fixed to the inlet-side line tube 202A and may be provided independently of the component sensor 311. For example, the line assembly portion may be a clip or a recessed portion capable of sandwiching the line tube. Alternatively, e.g., a strap with a hook-and-loop fastener may be wound around and fixed to the line tube.

In the present embodiment, the assembly target portion provided at the inlet-side line tube 202A is a portion between two branches 212, 213, but is not limited as long as the assembly target portion can be assembled with the line assembly portion. Depending on the configuration of the line assembly portion, a special configuration as the assembly target portion is not necessarily provided. Alternatively, the assembly target portion may be, e.g., a position indication indicating an assembly position. In a case where the assembly portion is, e.g., a clip, the assembly target portion may be a thick portion so that crushing of the line tube upon sandwiching can be reduced.

In the present embodiment, the branch 212 contacts the upper surface of the housing of the component sensor 311 as the line assembly portion, and does not move downwardly beyond such an upper surface. Thus, the branch 212 also functions as a movement restrictor that prevents the inlet-side line tube 202A from moving downwardly beyond the above-described upper surface. The movement restrictor is not limited to this configuration, and various configurations can be selected according to the configuration of the assembly portion. Alternatively, the assembly target portion may function as the movement restrictor. For example, if the line assembly portion is configured to sandwich the branch 212, the branch 212 functions as the assembly target portion and the movement restrictor. Note that the movement restrictor may be provided as necessary and is not necessarily provided.

Note that FIG. 5 shows such arrangement that the pump tube 201 is drawn in and out from the right side of the pump 300, but the pump tube 201 may be arranged so as to be drawn in and out from the left side of the pump 300.

The first tube holding portion 102A and the second tube holding portion 102B are arranged with an interval L1 therebetween such that the axial directions thereof are parallel with each other. The interval L1 is determined depending on the size of the pump 300, and in the case of a general dialysis monitoring device, is about 65 mm to 120 mm. The first tube holding portion 102A and the second tube holding portion 102B are attached to the pump such that the axial directions thereof are directions (horizontal direction) perpendicular to the vertical direction. With this configuration, there is almost no portion where blood flows diagonally downwardly in the pump tube 201. Thus, a situation where air bubbles remain in the pump tube 201 and a blood clot is caused accordingly is less likely to occur.

As shown in FIG. 2, a line-tube-side end 113 of the fixing plate 101 is not perpendicular to the axial directions of the first tube holding portion 102A and the second tube holding portion 102B, but is inclined to a pump tube 201 side from the second tube holding portion 102B side toward the first tube holding portion 102A side. Specifically, a length between the position of the line-tube-side end and the position of a line-tube-side end portion of the second tube holding portion 102B along the axial direction of the second tube holding portion 102B gradually increases from the second tube holding portion 102B side toward the first tube holding portion 102A side. Moreover, in the present embodiment, a pump-tube-side end 114 of the fixing plate 101 is not perpendicular to the axial directions of the first tube holding portion 102A and the second tube holding portion 102B, but is inclined. Such inclination is coincident with that of the line-tube-side end 113. That is, the fixing plate 101 is in the shape of a planar parallelogram.

As shown in FIG. 5, the inlet-side line tube 202A is drawn out downwardly from the pump 300 in the dialysis machine 400 provided with the line assembly portion below the pump 300. Since the line tube 202A is drawn out downwardly from the pump 300, the blood-return-side line tube 204 configured such that blood returned to the patient flows therein and extending downwardly from the drip chamber 211 and the inlet-side line tube 202A can be drawn side by side. In the layout as shown in FIG. 5, two blood-removal-side and blood-return-side line tubes can be drawn side by side with the minimum lengths, and the length of the entire extracorporeal circuit can be shortened. Arrangement of the line tubes needs to be easily visually checkable in order to prevent, e.g., an error in attachment, and the line tubes are preferably arranged so as not to cross each other. In this case, there is no crossing of the line tubes.

Meanwhile, the direction of the inlet-side line tube 202A needs to be changed in order to attach the pump tube 201 to the pump 300, but if the inlet-side line tube 202A is bent with a small curvature, the tube is crushed at the bent portion and kink leading to a difficulty in blood flow easily occurs. The tube holder 100 of the present embodiment is configured such that the line-tube-side end 113 of the fixing plate 101 is inclined to the pump tube 201 side from the second tube holding portion 102B side toward the first tube holding portion 102A side. Thus, when the tube holder 100 is attached with the second tube holding portion 102B side aligned with an end portion of a housing 302 of the pump 300, the first tube holding portion 102A side is closer to a rotor 301 side than the end portion of the housing 302 is to the rotor 301 side. Thus, the curvature of the inlet-side line tube 202A can be greater, and the kink is less likely to occur.

The line tube 202A can be arranged at a position apart from the pump 300 by increasing an internal between the pump 300 and the assembly position of the drip chamber 211, and accordingly, the curvature can be increased. However, in this case, the dialysis machine is increased in size, and the length of the entire extracorporeal circuit also increases. If the entirety of the tube holder 100 is positioned apart from the end portion of the housing 302, the pump 300 is increased in size, and as a result, the dialysis machine is increased in size. However, in the present embodiment, the line-tube-side end 113 of the fixing plate 101 is inclined to the pump tube side from the second tube holding portion 102B side toward the first tube holding portion 102A side. Thus, occurrence of the kink of the inlet-side line tube 202A can be reduced without a size increase in the dialysis machine.

In the present embodiment, the pump-tube-side end 114 of the fixing plate 101 is inclined as in the line-tube-side end 113, and therefore, the fixing plate 101 is in the shape of parallelogram. With this shape, the shape of the tube holder 100 can be simplified, and therefore, the tube holder 100 can be easily molded. Moreover, since the fixing plate 101 is in the shape of parallelogram, a strength of fixing the first tube holding portion 102A and the second tube holding portion 102B can be ensured while the area of the fixing plate is decreased. Note that the pump-tube-side end 114 may be inclined at an angle different from that of the line-tube-side end 113 and may be perpendicular to the axial directions of the first tube holding portion 102A and the second tube holding portion 102B. Note that the fixing plate 101 is easily formed in a case where the line-tube-side end 113 and the pump-tube-side end 114 are straight lines, but these ends may be curved lines.

In the present embodiment, the first tube holding portion 102A and the second tube holding portion 102B are arranged at positions shifted from each other in the axial direction. Thus, when the tube holder 100 is assembled with the housing 302 of the pump 300, an end portion of the line tube connection portion 122 of the first tube holding portion 102A is positioned inside (rotor 301 side) the housing 302 with respect to an end portion of the line tube connection portion 122 of the second tube holding portion 102B, and an end portion of the pump tube connection portion 121 of the second tube holding portion 102B is positioned outside the housing 302 with respect to an end portion of the pump tube connection portion 121 of the first tube holding portion 102A.

Since the positions of the end portions of the line tube connection portions 122 of the first tube holding portion 102A and the second tube holding portion 102B in the axial direction are shifted from each other, the degree of freedom in drawing of the inlet-side line tube 202A and the outlet-side line tube 202B is improved, and the layout of the dialysis machine is easily designed. For example, in the case of the dialysis machine 400 with the arrangement as shown in FIG. 5, the first tube holding portion 102A is shifted to the rotor 301 side as compared to the second tube holding portion 102B, therefore, a space for bending the line tube 202A with such a curvature that no kink occurs can be easily ensured.

A shift L2 in the axial direction on the line tube side and a shift L3 in the axial direction on the pump tube side between the first tube holding portion 102A and the second tube holding portion 102B are not particularly limited, but are preferably about 3.25 mm to 13.5 mm in terms of preventing a size increase in the device while reducing occurrence of the kink. Note that the length of the first tube holding portion 102A and the length of the second tube holding portion 102B are equal to each other in the present embodiment, and therefore, L2 and L3 are equal to each other. However, the length of the first tube holding portion 102A and the length of the second tube holding portion 102B may be different from each other, and in this case, L2 and L3 are different values.

The inside of the first tube holding portion 102A and the second tube holding portion 102B is not visible or difficult to be viewed, and for this reason, it is difficult to visually check air bubbles remaining in these portions. Thus, if the tube arrangement is adjusted by increasing the lengths of the tube holding portions in order to prevent the kink of the tube, the remaining air bubbles are less likely to be recognized. Particularly, on the lower first tube holding portion 102A side, the air bubbles easily remain, leading to a great problem. In the present embodiment, arrangement of the pump tube 201 and the line tube 202A is adjusted with the length of the first tube holding portion 102A set to the length of the second tube holding portion 102B or less, and therefore, the portion where the air bubbles are difficult to be visually checked can be decreased while occurrence of the kink is reduced.

In the present embodiment, since the inlet-side line tube 202A is drawn out downwardly and the outlet-side line tube 202B is horizontally drawn out, the position of the first tube holding portion 102A in the axial direction is shifted to the rotor 301 side. However, depending on the layout of the dialysis machine, the second tube holding portion 102B may be positioned closer to the rotor 301 side than the first tube holding portion 102A is to the rotor 301 side.

In the present embodiment, a clip portion 103 is provided on the outer edge of the fixing plate 101 on the first tube holding portion 102A side, and a thick rim 104 is provided on the outer edge of the fixing plate 101 on the second tube holding portion 102B side. The clip portion 103 and the rim 104 function as an attachment portion to be attached to an attachment target portion of the housing 302 of the pump 300. The rim 104 also has a function of enhancing the strength of the fixing plate 101. The rim 104 is provided with a positioning protrusion 141, and a positioning cutout 101*a* is provided in the line-tube-side end 113 of the fixing plate 101. The positioning protrusion 141 and the cutout 101*a* engage with a positioning configuration provided at the housing so that positioning of the tube holder 100 can be facilitated. Note that the positioning protrusion 141 may be provided as necessary and is not necessarily provided. Note that the mechanism for attaching the tube holder 100 to the housing 302 is not limited to above and various configurations can be employed.

In the present embodiment, the fixing plate 101 is a plate body having a constant width W1 smaller than the length W2 of the first tube holding portion 102A and the second tube holding portion 102B in the axial direction. With this configuration, the area of a portion, to which the fixing plate 101 is attached, of the pump 300 can be decreased, and the dialysis machine 400 can be compactified. Note that the fixing plate 101 may have any configuration as long as the first tube holding portion 102A and the second tube holding portion 102B can be held with a predetermined interval therebetween such that the axial directions thereof are parallel with each other.

The tube holder 100 of the present embodiment is configured such that the fixing plate 101 is molded integrally with the first tube holding portion 102A and the second tube holding portion 102B. In the case of molding a resin molded article, a pressable area is predetermined, and in order to achieve multi-cavity molding for molding a plurality of molded articles at once, the area of a cavity as viewed in a press direction needs to be as small as possible. For this reason, a vertical mold separatable into a pump-tube-side portion and a line-tube-side portion is preferably used.

In the case of a horizontal mold configured such that the principal surface of the fixing plate 101 is arranged in a direction perpendicular to the press direction, the area of a cavity necessary for molding one molded article as viewed in the press direction is an area including a side shape shown in FIG. 2. There is no choice but to employ such a configuration in order to take out the molded article in a case where a tubular first tube connector and a tubular second tube connector are arranged such that the extensions thereof cross each other. However, in the case of the tube holder 100 of the present embodiment, since the two tubular first tube holding portion 102A and second tube holding portion 102B are parallel with each other, the principal surface of the fixing plate 101 is arranged parallel with the press direction, and the molded article can be taken out of the mold even in the case of the vertical mold separatable into the pump-tube-side portion and the line-tube-side portion. The area of the cavity necessary for molding one molded article as viewed in the press direction in the case of the vertical mold is an area including a front shape shown in FIG. 3, and is extremely smaller than that in the case of the side shape. Thus, as compared to the case of the horizontal mold, the number of articles molded from the same mold area can be greater, and production efficiency and cost can be greatly reduced.

On the other hand, in the case of a mold separable perpendicularly to the axes of the first tube holding portion 102A and the second tube holding portion 102B, an unbalance shape greatly different in a cavity depth between the first tube holding portion 102A side and the second tube holding portion 102B side is formed. With a poor cavity balance, a molding defect easily occurs due to non-uniformity of a resin flow, and the molded article is difficult to be taken out of the mold.

In the present embodiment, as shown in FIG. 2, a parting line PL has a first perpendicular line 117 and a second perpendicular line 119 extending in a direction perpendicular to the axes of the first tube holding portion 102A and the second tube holding portion 102B and an inclined line 118 extending in a direction inclined with respect to the axes of the first tube holding portion 102A and the second tube holding portion 102B. The first perpendicular line 117 divides the first tube holding portion 102A into the pump tube side and the line tube side, the second perpendicular line 119 divides the second tube holding portion 102B into the pump tube side and the line tube side, and the inclined line 118 connects the first perpendicular line 117 and the second perpendicular line 119 to each other in the fixing plate 101. Thus, the cavity depth can be substantially the same between the first tube holding portion 102A side and the second tube holding portion 102B side, and therefore, moldability and releasability can be improved.

The position of the parting line PL is not particularly limited, but in terms of easy mold production and moldability improvement, the first perpendicular line 117 and the second perpendicular line 119 preferably pass through the vicinity of a boundary between the pump tube connection portion 121 and the line tube connection portion 122.

In the present embodiment, the fixing plate 101 has, on the line tube side with respect to the parting line PL, an angle changing portion 112 having such a tapered surface that the thickness thereof gradually decreases toward the line tube side. With the angle changing portion 112, the line-tube-side mold portion can be easily released from the cavity. Thus, when the mold is opened, the molded article can remain on the pump tube side, and productivity can be greatly improved.

The taper angle of the angle changing portion 112 is not particularly limited, but is preferably about 0.1° to 3° in terms of the releasability. A pump-tube-side end portion of the angle changing portion 112 preferably extends, in terms of easy mold production, in a direction perpendicular to the axial directions of the first tube holding portion 102A and the second tube holding portion 102B, but may be slightly tapered. In this case, the taper angle of the angle changing portion 112 toward a line-tube-side end portion is preferably great. The angle changing portion 112 is preferably configured such that both sides of the fixing plate 101 are symmetrically inclined, but an inclination angle may be different between these sides or only one side may be inclined. A portion 111 of the fixing plate 101 other than the angle changing portion 112 may have a constant thickness, but the thickness may change such that the portion 111 is inclined at an angle different from that of the angle changing portion 112.

The dialysis machine shown in FIG. 5 is provided with the attachment target portion, to which the tube holder 100 is attached, on the right side of the rotor 301 of the pump 300 provided on the side surface of the housing, and the line tubes 202A, 202B are drawn out rightward from the pump 300. However, depending on the installation location of the dialysis machine, the line tubes are preferably drawn out leftward from the pump. For this reason, there are dialysis machines configured such that an attachment target portion is positioned on the left side of a rotor. Conventionally, an extracorporeal circuit having a tube holder attachable to an attachment target portion positioned on the right side of a rotor and an extracorporeal circuit having a tube holder attachable to an attachment target portion positioned on the left side of a rotor have been separately prepared.

The tube holder 100 of the present embodiment is attached, with the attachment portion including the clip portion 103 and the rim 104, to the attachment target portion provided on the device side. As shown in FIG. 3, the tube holder 100 has a structure plane-symmetry with respect to the fixing plate 101 in a thickness direction, and even when the tube holder 100 is turned back, the configuration in the thickness direction does not change. Thus, when a first surface of the fixing plate faces the device side, the clip portion and the rim function as a first attachment portion for attachment to a first attachment target portion. On the other hand, when a second surface of the fixing plate opposite to the first surface faces the device side, the clip portion and the rim function as a second attachment portion for attachment to a second device that attaches the tube holder to the left side of the rotor. Thus, one type of extracorporeal circuit is applicable to any of a dialysis machine configured such that a pump is laid out on the right side and a dialysis machine configured such that a pump is laid out on the left side.

Since the tubular holder has the plane symmetrical structure and the first attachment portion and the second attachment portion are the same as each other, the same pump can be used not only for a first device but also for a second device only by inverting the orientation of the pump. However, the first attachment portion and the second attachment portion may be separately provided, a first pump having a first attachment target portion corresponding to the first attachment portion is provided in the first device, and a second pump having a second attachment target portion corresponding to the second attachment portion may be provided in the second device. Alternatively, the pump may be configured such that the first attachment target portion and the second attachment target portion are integrated with the rotor, but the first attachment target portion and the second attachment target portion may be separated from the rotor.

In the present embodiment, the fixing plate 101 has raised portions 106 protruding from a center portion in the thickness direction. The dialysis machine is provided with pushing pins for pushing the raised portions 106, and therefore, the tube holder 100 can be automatically detached from the pump. With the raised portions 106, the length of the pushing pin can be shortened as compared to the case of pushing the fixing plate 101 itself by the pushing pins.

In the present embodiment, the raised portion 106 is formed in a hollow dome shape opened on one side and closed by a curved surface on the other side in the axial directions of the first tube holding portion 102A and the second tube holding portion 102B. Since the raised portion 106 is formed in the hollow dome shape, the raised portion 106 can be formed without increasing the thickness thereof, and therefore, e.g., occurrence of sink marks upon molding can be reduced. Moreover, since the raised portion 106 is in the shape closed on the other side, the strength thereof can be increased as compared to a shape opened on both sides. Further, since the raised portion 106 is closed by the curved surface, occurrence of distortion can be reduced. In addition, since the raised portion 106 is formed along the axial directions of the first tube holding portion 102A and the second tube holding portion 102B, a mold is not complicated even for the hollow structure.

The raised portion 106 also functions as a rib for reducing occurrence of warpage of the fixing plate 101. After a blood circuit has been assembled with the tubes connected to the tube holder 100, such a circuit is sterilized and stored. If the fixing plate 101 warps while being stored, it is difficult to attach the fixing plate 101 to the pump 300. Since the raised portions 106 are provided on the center portion of the fixing plate 101, warpage of the fixing plate 101 can be reduced and be stored for a long period of time.

When the fixing plate 101 is attached to the housing 302 of the pump 300, the fixing plate 101 can be attached smoother when deformed so as to slightly bend. The fixing plate 101 is deformed back to an original state when the tube holder 100 is correctly attached, so that it can be checked, from a feeling upon attachment, whether or not the tube holder 100 has been correctly attached and operability can be improved. However, if the fixing plate 101 is extremely easily bendable, the fixing plate 101 is extremely deformed, is not deformed back to the original shape, or is easily detached after attachment.

In the present embodiment, the center portion of the fixing plate 101 provided with the raised portions 106 as the ribs is a less-bendable portion where the fixing plate 101 is less bendable, and a portion of the fixing plate 101 between the raised portion 106 and each of the first tube holding portion 102A and the second tube holding portion 102B is an easily-bendable portion where the fixing plate 101 is more easily bendable than the less-bendable portion. Thus, moderate deformability can be provided to the fixing plate 101. Note that in the present embodiment, the less-bendable portion is provided at the center portion of the fixing plate 101 and the portions on both sides of the less-bendable portion are the easily-bendable portions, but the operability can be improved as long as the easily-bendable portion is provided at the periphery of at least one of the first tube holding portion 102A or the second tube holding portion 102B. Thus, the raised portion 106 may further extend to the first tube holding portion 102A side or the second tube holding portion 102B side, for example.

Figure 6:
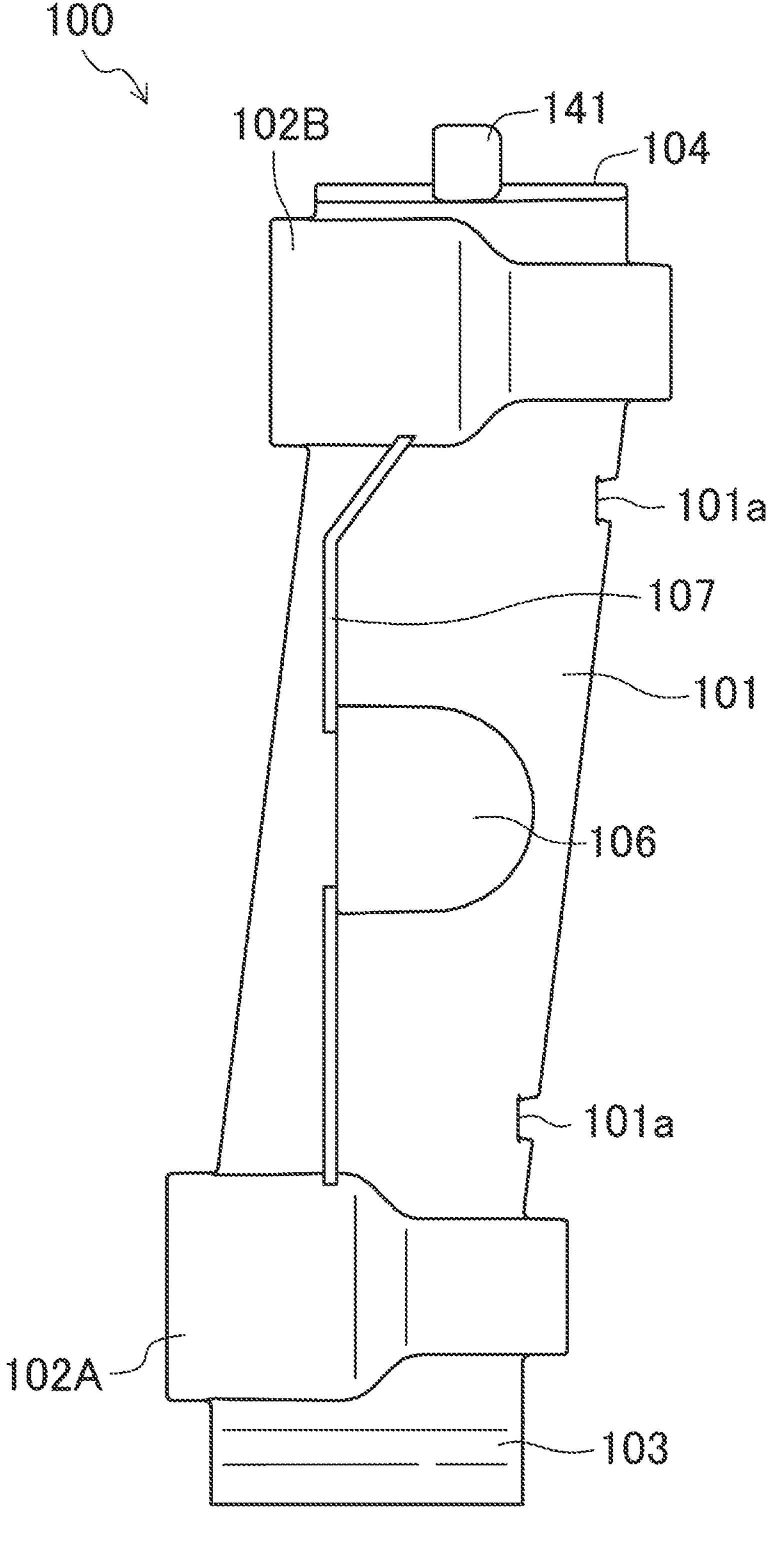
FIG. 6 is a plan view showing a variation of the pump tube holder.

The fixing plate 101 may be a flat plate without the raised portions 106, and may also be provided with, e.g., a reinforcement rib. For example, as shown in FIG. 6, ribs 107 may be formed in a direction of connecting the first tube holding portion 102A and the second tube holding portion 102B to each other. It is required that the fixing plate 101 is elastically deformable to some extent upon attachment to the pump 300. Since the ribs 107 are provided in the direction of connecting the first tube holding portion 102A and the second tube holding portion 102B to each other, the fixing plate 101 can be elastically deformable while warpage upon storage is reduced. The ribs 107 may be in the shape of a straight line connecting the first tube holding portion 102A and the second tube holding portion 102B to each other, but with bent portions, occurrence of warpage can be further reduced.

In the case of the plane symmetrical structure in the thickness direction, the raised portions 106 and the ribs 107 may be provided on both surfaces of the fixing plate 101. Note that the raised portions 106 and the ribs 107 may be provided as necessary, and only one raised portion 106 and one rib 107 may be provided or no raised portions 106 and ribs 107 may be provided. The example where the rib 107 is provided entirely between the raised portion 106 and each of the first tube holding portion 102A and the second tube holding portion 102B has been described, but the rib 107 may be provided only partially between the raised portion 106 and each of the first tube holding portion 102A and the second tube holding portion 102B.

In the present embodiment, the pump tube 201 and the line tubes 202A, 202B are fitted in the first tube holding portion 102A and the second tube holding portion 102B, and accordingly, are connected to each other. By such fitting and connection, e.g., a step in the connection portion can be reduced, and therefore, e.g., blood accumulation is less likely to occur. Moreover, an assembly step of connecting each tube to the holder can be easily automated. Note that the pump tube 201 and the line tubes 202A, 202B may be fitted onto the first tube holding portion 102A and the second tube holding portion 102B.

The example where the first tube holding portion and the second tube holding portion also have a connector function of connecting the pump tube and the line tubes to each other has been described, but the first tube holding portion and the second tube holding portion may only hold the tubes without the connector function. In this case, the pump tube and the line tubes may be connected to each other through separately-provided connectors, or may be directly connected to each other without connectors. The first tube holding portion and the second tube holding portion may hold connector portions where the pump tube and the line tubes are connected to each other.

The tube holder 100 can be attached to the pump 300 by the attachment portion including the clip portion 103 and the rim 104 and the attachment target portion provided on the device side. The clip portion 103 is formed so as to protrude to the side (outwardly) opposite to the second tube holding portion 102B from the first tube holding portion 102A, and a tubular body with a cutout extends along the axial direction of the first tube holding portion 102A. The rim 104 is a thick portion formed so as to protrude to the side (outwardly) opposite to the first tube holding portion 102A from the second tube holding portion 102B.

The attachment target portion includes a clip portion insertion groove 351 and a rim insertion groove 352 formed in the housing 302 of the pump 300. In the device of the present embodiment, the clip portion insertion groove 351 is formed in a lower side wall 302A of the housing 302, and the rim insertion groove 352 is formed in an upper side wall 302B of the housing 302.

The clip portion 103 is inserted into the clip portion insertion groove 351 in such a manner that two curved walls thereof are compressed, and engages with the clip portion insertion groove 351 with moderate friction. Thus, the tube holder 100 can turn about the clip portion 103 inserted into the clip portion insertion groove 351.

The length of a narrowest portion between the clip portion insertion groove 351 and the upper side wall 302B is slightly shorter than a length between the clip portion 103 and the rim 104. Thus, when the tube holder 100 turns with the clip portion 103 as the point of support, the rim 104 contacts the upper side wall 302B of the housing 302. Since the fixing plate 101 of the tube holder 100 is slightly bendable, the rim 104 can be fitted in the rim insertion groove 352 beyond the contact portion and be locked. In this manner, the tube holder 100 is fixed to the housing 302 of the pump 300.

In the present embodiment, the length W1 of the clip portion 103 and the length W3 of the clip portion insertion groove 351 are substantially the same as each other. Similarly, the lengths of the rim 104 and the rim insertion groove 352 are substantially the same as each other. Thus, almost no movement of the tube holder 100 fixed to the housing 302 is made to the front side (rotor 301 side) and the back side. Consequently, even when the pump 300 is driven by rotation of the rotor 301, almost no front-back rattling of the tube holder 100 occurs.

When the tube holder 100 of the present embodiment is attached to the housing, the clip portion 103 formed on the first tube holding portion 102A side is first inserted into clip portion insertion groove 351. Thus, a portion of the pump tube 201 on the first tube holding portion 102A side is on a far side (bottom side of the housing 302) with respect to rotor pins 305 of the rotor 301. Next, by rotation of the rotor 301, the rotor pin 305 presses the pump tube 201 from the first tube holding portion 102A side, and pushes the pump tube 201 into a clearance between the rotor 301 and the housing 302. Thereafter, the rim 104 formed on the second tube holding portion 102B side is fitted and locked in the rim insertion groove 352.

In terms of the rotor pin 305 of the rotor 301 reliably pressing the pump tube 201, the clip portion 103 as the attachment portion on the first tube holding portion 102A side is preferably attached as close as possible to the rotor 301. On the other hand, when the rotor pin 305 presses a portion of the pump tube 201 on the second tube holding portion 102B side, if the tube holder 100 is close to the rotor 301, the pump tube 201 is greatly curved at the portion where the rotor pin 305 contacts the pump tube 201. For this reason, there is a probability that friction resistance between the rotor pin 305 and the pump tube 201 increases and the pump tube 201 is damaged or automatic attachment of the pump tube is stopped due to stop of the rotor 301.

The tube holder 100 of the present embodiment is configured such that by positioning the front end of the rim 104 on the back side with respect to the front end of the clip portion 103 attached first, the rim 104 side has a distance from the rotor 301 even when the clip portion 103 approaches the rotor 301. With this configuration, the rotor pin 305 can press the portion of the pump tube 201 on the first tube holding portion 102A side, and the damage of the pump tube 201 can be reduced by a decrease in the curvature of the pump tube 201.

After the pump tube 201 has been attached to the rotor 301, when the rim 104 is fitted in the rim insertion groove 352 by turning the tube holder 100 about the clip portion 103, a portion of the pump tube 201 between the rotor 301 and the second tube holding portion 102B is slightly deformed. In the present embodiment, the portion of the pump tube 201 between the rotor 301 and the second tube holding portion 102B can be relatively long, and therefore, force required for such deformation can be reduced. Thus, the rim 104 can be smoothly fitted in the rim insertion groove 352.

Moreover, since the portion of the pump tube 201 between the rotor 301 and the second tube holding portion 102B is relatively long, an effect of absorbing force generated by the rotor pump and greatly fluctuating periodically can be enhanced. Thus, force on the rim 104 can be reduced upon operation of the pump 300, and therefore, there is no need to increase engagement force between the rim 104 and the rim insertion groove 352 and the rim 104 can be fitted in the rim insertion groove 352 with a hand or be disengaged from the rim insertion groove 352 with the pushing pins.

In the present embodiment, the pump tube 201 held on the first tube holding portion 102A is strongly pulled upon a normal pump operation of rotating the rotor 301 forward. On the other hand, force is applied to the pump tube 201 held on the second tube holding portion 102B in a direction of pushing out the pump tube 201 by the forward-rotating rotor 301. Thus, force on the attachment portion and the attachment target portion is smaller on the second tube holding portion 102B side than the first tube holding portion 102A side. For this reason, the attachment portion and the attachment target portion on the first tube holding portion 102A side preferably engage with each other stronger than the attachment portion and the attachment target portion on the second tube holding portion 102B side. On this point, the tube holder 100 of the present embodiment is preferred, in which the clip portion 103 whose engagement force is easily increased is formed on the first tube holding portion 102A side and the easily-detachable rim 104 is formed on the second tube holding portion side.

In the present embodiment, the outer surfaces of the two walls of the clip portion 103 are formed in a smooth curved shape. Thus, the clip portion 103 inserted into the clip portion insertion groove 351 can be smoothly turned. On the other hand, the inner surfaces of the two walls of the clip portion 103 are formed with bent portions. Thus, snapping force of the two walls increases, and accordingly, engagement force with the clip portion insertion groove 351 increases. As a result, a situation where the clip portion 103 accidentally drops from the clip portion insertion groove 351 is less likely to occur. Note that the clip portion 103 is not limited to this configuration and various configurations can be employed.

The tube holder 100 of the present embodiment is configured such that the raised portions 106 are formed on the center portion of the fixing plate 101 and the rim 104 and the rim insertion groove 352 are disengaged from each other by pressing the raised portions 106 by the pushing pins 355 formed on the pump 300. The contact positions of the pushing pins 355 are the center portion of the fixing plate 101, and therefore, the fixing plate 101 can be bent and the rim 104 and the rim insertion groove 352 can be more easily disengaged from each other. As compared to the case of pushing an upper end portion of the tube holder 100, the length of pushing by the pushing pin 355 can be shortened.

In the present embodiment, since the raised portions 106 are formed on the center portion of the fixing plate 101, the length of pushing by the pushing pin 355 can be further shortened. Moreover, since the raised portions 106 also have the reinforcement effect, a situation where the fixing plate 101 is damaged by the pushing pins 355 is less likely to occur.

The tube holder 100 whose rim 104 is disengaged from the rim insertion groove 352 by pushing by the pushing pins 355 turns about the clip portion 103, and the second tube holding portion 102B side is pushed out to the near side of the device such that the tube holder 100 is inclined. In this state, by reverse rotation of the rotor 301, the rotor pin 305 moves, on the second tube holding portion 102B side, to the far side of the pump tube 201, and accordingly, the pump tube 201 is drawn out from the clearance between the rotor 301 and the housing 302 and the pump tube 201 and the rotor 301 are disengaged from each other. By pulling the tube holder 100 with the hand in a state in which the pump tube 201 and the rotor 301 are disengaged from each other, the clip portion 103 is pulled out of the clip portion insertion groove 351, and the tube holder 100 can be detached.

In the present embodiment, the pump tube connection portion 121 of the second tube holding portion 102B functions as a sensor driver that drives a sensor pin 356 of a tube holder attachment sensor that detects that the rim 104 is inserted into the rim insertion groove 352 and the tube holder 100 is fixed to the housing 302. The second tube holding portion 102B is a portion having a great displacement between a state of the rim 104 being inserted into the rim insertion groove 352 and a state of the rim 104 being disengaged from the rim insertion groove 352. Thus, since the second tube holding portion 102B is used as the sensor driver, detection on whether or not the tube holder 100 is attached can be facilitated. The large-diameter pump tube connection portion 121 is positioned closest to the device side when the rim 104 is inserted into the rim insertion groove 352. Thus, detection can be made without the sensor pin 356 greatly protruding from the device side, and therefore, failure and damage of the tube holder attachment sensor are less likely to occur.

Figure 8:
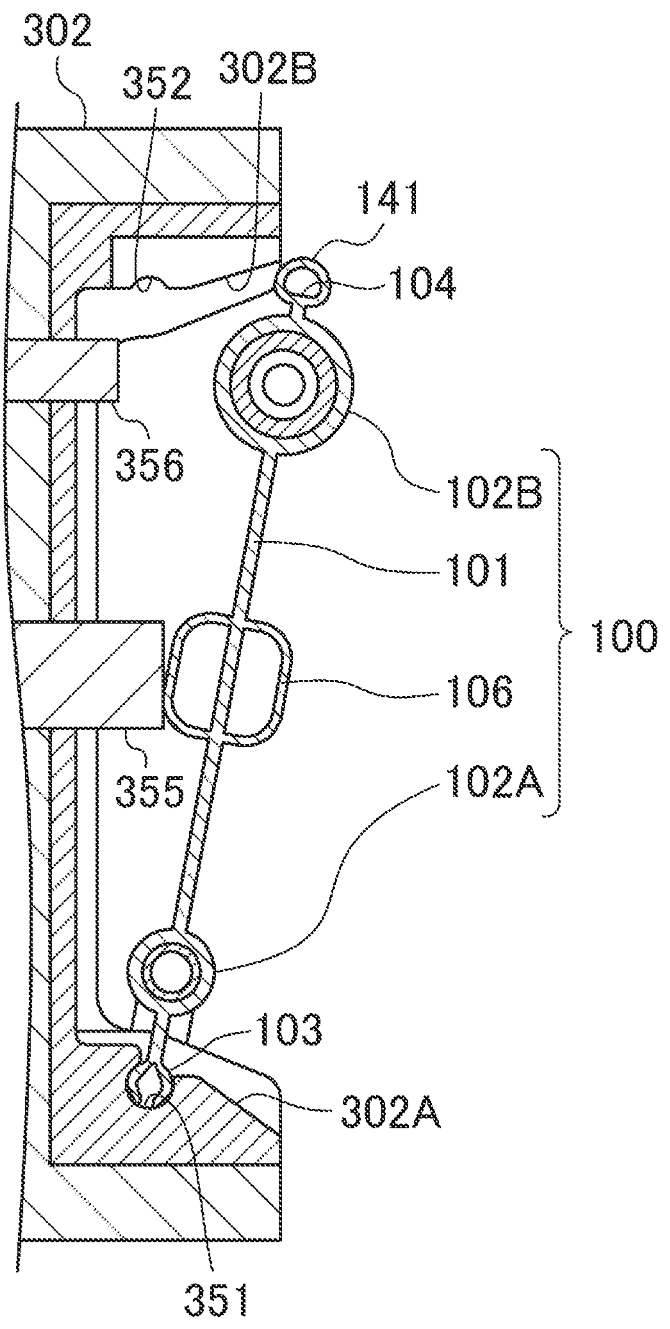
FIG. 8 is a sectional view taken along VIII-VIII line in FIG. 7 in a state in which the pump tube holder is pushed by a pushing pin.

FIG. 8 shows, as the tube holder attachment sensor, a sensor of a sensor pin pushing type, but the tube holder attachment sensor is not limited to this sensor and various configurations can be employed as long as it can be checked whether or not the tube holder 100 is attached and locked to the housing 302.

When the pump tube 201 is stored for a long period of time with attached to the tube holder 100 with a loop having a small curvature radius, there is a probability that the tube is deteriorated and bent. The pump tube 201 is held in a twisted state between the first tube holding portion 102A and the second tube holding portion 102B so that the direction of stress on the pump tube 201 can be shifted and occurrence of bending due to long-term storage can be reduced.

A method for holding the pump tube 201 in the twisted state between the first tube holding portion 102A and the second tube holding portion 102B is not particularly limited, but for example, one end portion of the pump tube 201 is fixed to the second tube holding portion 102B and is subsequently fixed to the first tube holding portion 102A with the other end of the pump tube 201 twisted. In terms of preventing bending of the pump tube 201 while reducing influence of a stress increase by twisting, the twist angle of the pump tube 201 is preferably 20° or more and 150° or less and more preferably 30° or more and 100° or less.

The twist angle of the pump tube 201 is determined according to a positional relationship between a reference point of the end portion of the pump tube 201 fixed to the second tube holding portion 102B and a comparison point of the end portion of the pump tube 201 fixed to the first tube holding portion 102A. The reference point is an arbitrary point of the end portion of the pump tube 201 fixed to the second tube holding portion 102B, and the comparison point is such a point of the end portion of the pump tube 201 fixed to the first tube holding portion 102A that a distance to the reference point along an outer peripheral surface is the shortest in a case where no force is on the pump tube 201. For example, in a case where a point closest to the first tube holding portion 102A side on the end portion of the pump tube 201 fixed to the second tube holding portion 102B is the reference point, if the other end of the pump tube 201 is fixed to the first tube holding portion 102A with a twist angle of 0°, the comparison point is a position closest to the second tube holding portion 102B side. If the other end of the pump tube 201 is fixed with a twist angle of 180°, the comparison point is positioned farthest from the second tube holding portion 102B side.

Figure 9:
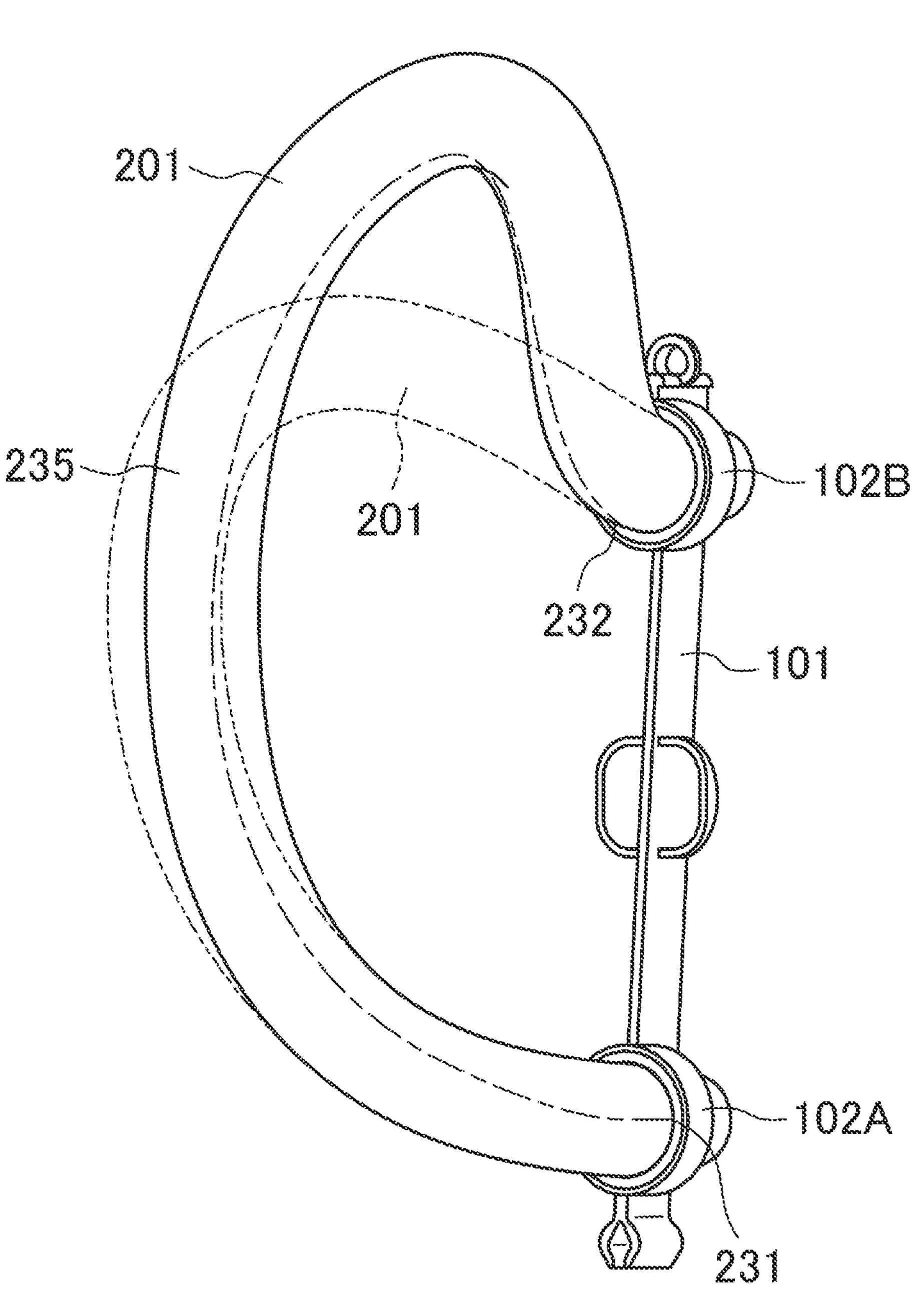
FIG. 9 is a perspective view showing one example of a pump tube holding state.
Figure 10:
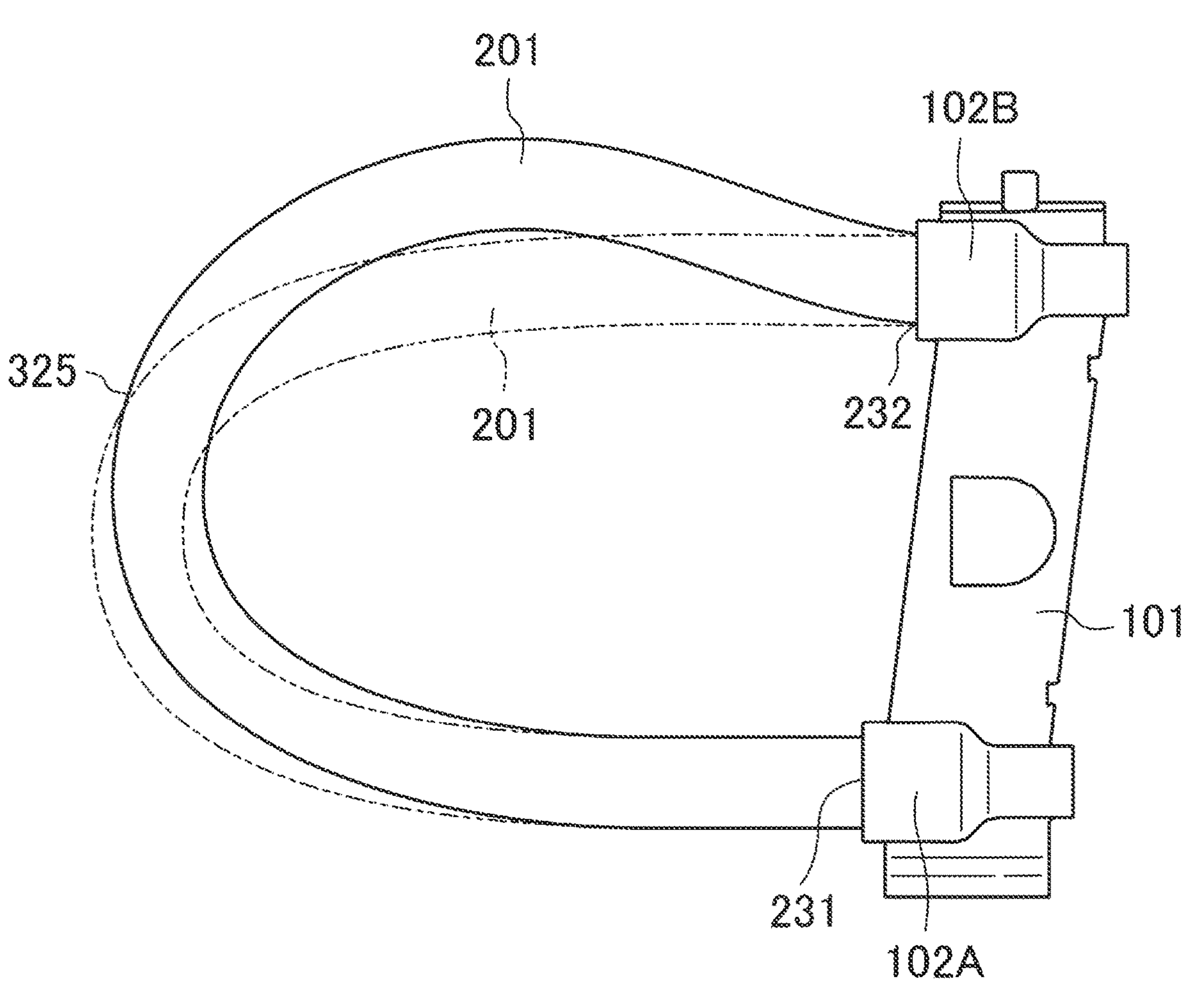
FIG. 10 is a plan view showing one example of the pump tube holding state.

FIGS. 9 and 10 show a state in which the pump tube 201 is held between the first tube holding portion 102A and the second tube holding portion 102B with a twist angle of 90°. In FIGS. 9 and 10, the twist angle is 90°, and the pump tube 201 is rotated clockwise by 90° as viewing the first tube holding portion 102A from the pump tube 201 side. In this case, a reference point 232 on the second tube holding portion 102B side is positioned closest to the first tube holding portion 102A side, and a comparison point 231 on the first tube holding portion 102A side is positioned on the right side of the first tube holding portion 102A as viewing the first tube holding portion 102A from the pump tube 201 side.

Figure 7:
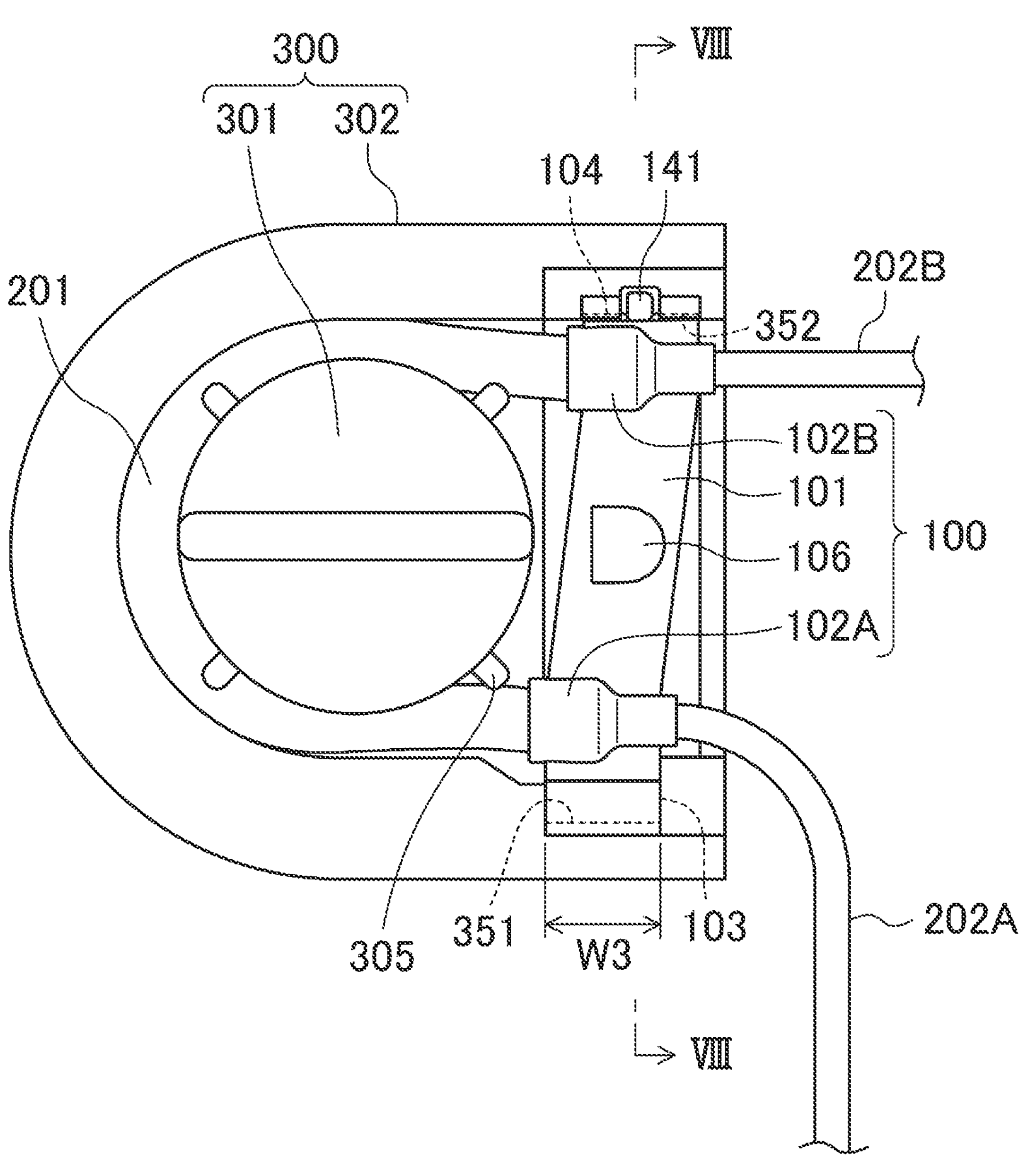
FIG. 7 is a view showing a state in which an attachment portion of the pump tube holder is attached to an attachment target portion of a housing.

In a case where the pump tube 201 is fixed with twisted in the above-described direction, the loop of the pump tube 201 is shifted rightward as viewing the first tube holding portion 102A from the pump tube 201 side as compared to a case where the twist angle is 0° as indicated by a chain double-dashed line in FIGS. 9 and 10. Moreover, the loop shift is greater on the second tube holding portion 102B side with respect to an intermediate portion of the pump tube 201 than on the first tube holding portion 102A side. In this case, when the pump tube 201 is attached to the pump 300 as shown in FIG. 7, the rotor pin 305 can smoothly push in the pump tube 201 on the first tube holding portion 102A side. Moreover, when the pump tube 201 is detached, the rotor pin 305 can smoothly move under the pump tube 201. Note that the direction of twist of the pump tube 201 may be the opposite direction.

Figure 11:
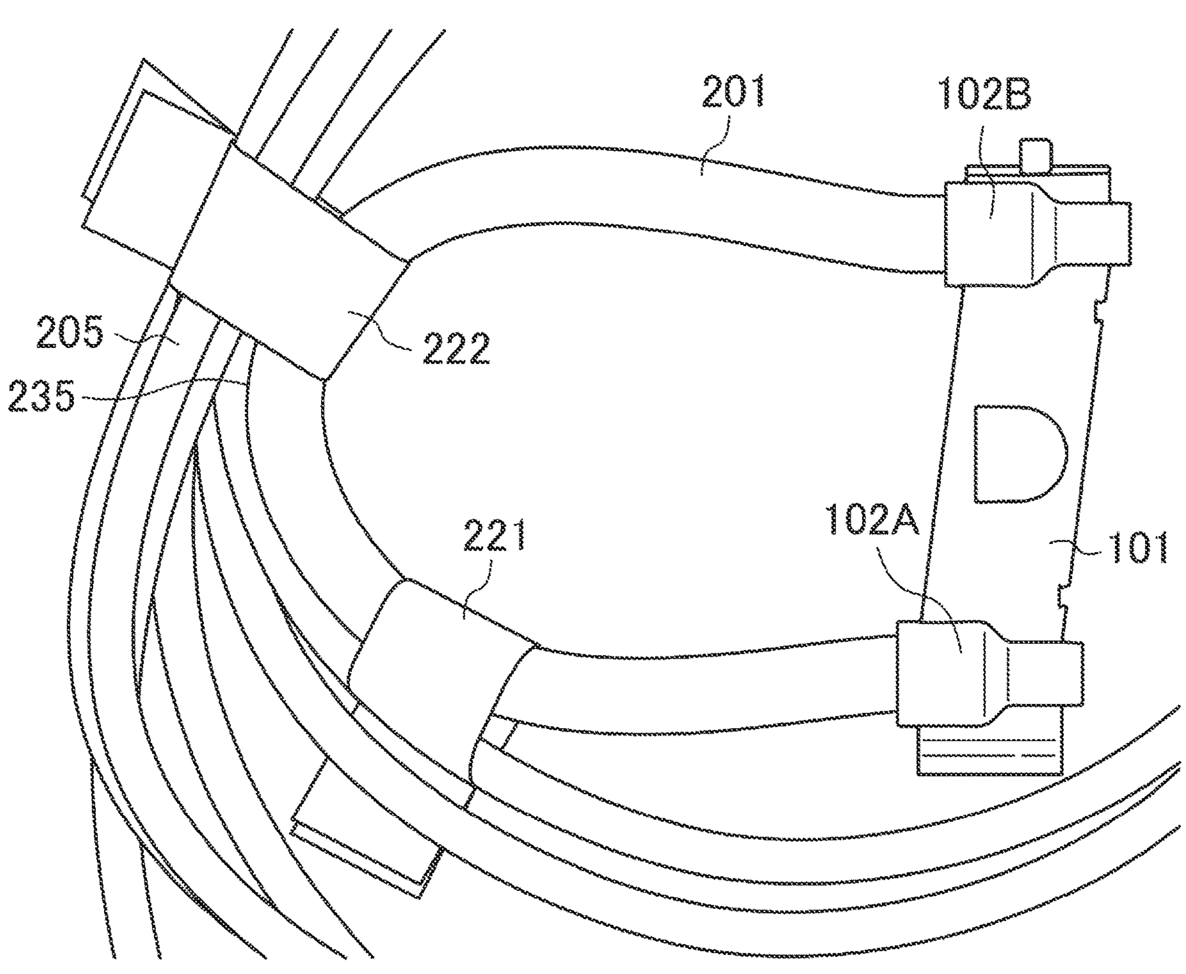
FIG. 11 is a plan view showing one example of an extracorporeal circuit storage state.

When the extracorporeal circuit manufactured by assembling, e.g., the pump tube 201 and the line tubes to the tube holder 100 is stored and transported, the pump tube 201 may be bundled with line tubes 205 other than the pump tube 201 using bundling portions 221, 222, as shown in FIG. 11. Since the pump tube 201 is bundled with the line tubes 205, force acting in a direction of bending the pump tube 201 can be dispersed, and therefore, bending of the pump tube 201 is less likely to occur even upon long-term storage.

The bundling portions 221, 222 are preferably attached such that at least part thereof is positioned on both sides of a loop inflection position (top position) 235 of the loop of the pump tube 201. With this configuration, the loop of the pump tube 201 can be pulled outwardly, and therefore, an effect of relieving the force in the bending direction can be greater.

In FIG. 11, the bundling portions 221, 222 are tapes, but various configurations such as clips can be employed as long as the pump tube 201 can be bundled with the other line tubes 205. The line tubes 205 bundled with the pump tube 201 may be those arrangeable at the position of the pump tube 201 among extracorporeal circuit tubes wound in a greater loop shape. Moreover, the line tubes 205 are not limited to those coupled to the pump tube 201, and independent tubes used as a set may be used. The line tubes 205 are not limited to the tubes, and the pump tube 201 may be fixed to, e.g., a tray for packaging. Using a member for supporting the pump tube 201 from the outside, bending of the pump tube 201 can also be reduced. For example, the pump tube 201 may be housed in an outer tube member, or a shape retention buffer may be sandwiched in the loop of the pump tube 201.

The extracorporeal circuit can be packaged and stored with the pump tube 201 bundled. Moreover, in this state, the extracorporeal circuit can be sterilized.

FIGS. 9 to 11 show the example where the pump tube 201 is attached to the tube holder 100 configured such that the first tube holding portion 102A and the second tube holding portion 102B are arranged at the positions shifted from each other in the front-back direction. However, the problem leading to bending of the pump tube 201 may be caused even in the case of using a tube holder other than the tube holder having the above-described configuration. The configuration in which bending of the pump tube 201 is less likely to occur as shown in FIGS. 9 to 11 is also applicable to other extracorporeal circuits different in a tube holder configuration.

INDUSTRIAL APPLICABILITY

The extracorporeal circuit of the present disclosure can solve at least one of various problems caused in an extracorporeal circuit in which a tube is attached to a pump through a holder, and is useful in a medical field including hemodialysis.

DESCRIPTION OF REFERENCE CHARACTERS

100 Tube Holder
101 Fixing Plate
102A First Tube Holding Portion
102B Second Tube Holding Portion
103 Clip Portion
104 Rim
106 Raised Portion
107 Rib
112 Angle Changing Portion
113 Line-Tube-Side End
114 Pump-Tube-Side End
117 First Perpendicular Line
118 Inclined Line
119 Second Perpendicular Line
121 Pump Tube Connection Portion
122 Line Tube Connection Portion
123 Tapered Portion
141 Positioning Protrusion
201 Pump Tube
202A Line Tube
202B Line Tube
203 Line Tube
204 Line Tube
205 Line Tube
211 Drip Chamber
212 Branch
213 Branch
221 Bundling Portion
222 Bundling Portion
231 Comparison Point
232 Reference Point
235 Inflection Position
300 Pump
301 Rotor
302 Housing
302A Lower Side Wall
302B Upper Side Wall
305 Rotor Pin 311 Component Sensor
312 Liquid Level Sensor
313 Bubble Sensor
321 Port
351 Clip Portion Insertion Groove
352 Rim Insertion Groove
355 Pushing Pin
356 Sensor Pin
400 Dialysis machine

The invention claimed is:

1. An extracorporeal circuit assembled with a dialysis machine having a pump portion provided on a side surface of a housing, the pump portion having a rotor and a pump housing, the extracorporeal circuit comprising:
a pump tube assembled with the rotor of the pump portion;
a line tube; and
a tube holder holding the pump tube and the line tube,
wherein the tube holder has first and second tube holding portions holding the pump tube in a loop shape and holding the line tube and a fixing plate coupling the first tube holding portion and the second tube holding portion to each other, and
wherein, when the tube holder is attached to the pump housing, the fixing plate is configured such that a side end of opposite to the rotor thereof is inclined to the rotor side from the second tube holding portion toward the first tube holding portion.

2. The extracorporeal circuit of claim 1, wherein, when the tube holder is attached to the pump housing:
a line-tube-side end portion of the first tube holding portion is positioned closer to the rotor side than a line-tube-side end portion of the second tube holding portion is to the rotor side, and
a pump-tube-side end portion of the first tube holding portion is positioned closer to the rotor side than a pump-tube-side end portion of the second tube holding portion is to the rotor side.

3. The extracorporeal circuit of claim 2, wherein
the line tube has a movement restrictor that restricts downward movement of the line tube.

4. The extracorporeal circuit of claim 1, wherein the tube holder has an attachment portion attached to an attachment target portion provided on the dialysis machine, and
wherein the attachment portion is attached to the dialysis machine that is configured such that the rotor and the attachment target portion are in a first positional relationship in a state in which a first surface of the fixing plate faces the dialysis machine side and is attached to the dialysis machine that is configured such that the rotor and the attachment target portion are in a second positional relationship opposite to the first positional relationship in a state in which a second surface of the fixing plate faces the dialysis machine side.

5. An extracorporeal circuit assembled with a dialysis machine having a pump portion on a side surface of a housing, the pump portion having a rotor and a pump housing, the extracorporeal circuit comprising:
a pump tube assembled with the rotor of the pump portion;
a line tube; and
a tube holder holding the pump tube and the line tube and detachably attachable to the pump housing,
wherein the tube holder has first and second tube holding portions holding the pump tube in a loop shape and holding the line tube and a fixing plate coupling the first tube holding portion and the second tube holding portion to each other, and
wherein the fixing plate has a side end opposite to the rotor inclined to the rotor side from the second tube holding portion side toward the first tube holding portion side when the tube holder is attached to the pump housing, and has a less-bendable portion provided with a rib and an easily-bendable portion provided between the less-bendable portion and at least one of the first tube holding portion or the second tube holding portion, the easily-bendable portion of the fixing plate being more easily bendable than the less-bendable portion.

6. The extracorporeal circuit of claim 5, wherein
the tube holder has a parting line between a pump-tube-side mold portion and a line-tube-side mold portion, and
the fixing plate has an angle changing portion on a line tube side with respect to the parting line, and the angle changing portion has such a tapered surface that a thickness thereof gradually decreases toward the line tube side.

7. The extracorporeal circuit of claim 5, wherein
the tube holder has a parting line between a pump-tube-side mold portion and a line-tube-side mold portion, and
the parting line has an inclined line extending in a direction inclined with respect to axial directions of the first tube holding portion and the second tube holding portion.

8. An extracorporeal circuit assembled with a dialysis machine having a pump portion on a side surface of a housing, the pump portion having a rotor and a pump housing, the extracorporeal circuit comprising:
a pump tube assembled with the rotor of the pump portion;
a line tube; and
a tube holder holding the pump tube and the line tube and detachably attached to the pump housing,
wherein the tube holder has first and second tube holding portions, a fixing plate coupling the first tube holding portion and the second tube holding portion to each other, a first attachment portion formed so as to protrude to a side opposite to the second tube holding portion from the first tube holding portion, and a second attachment portion formed so as to protrude to a side opposite to the first tube holding portion from the second tube holding portion,
wherein the line tube is attached to a back side of the first tube holding portion and the second tube holding portion, and the pump tube is attached to a front side in a loop shape such that blood is delivered from the first tube holding portion to the second tube holding portion,
wherein the first attachment portion is turnably attached to a first attachment target portion which is a groove extending in a front-to-back direction and formed in a lower side wall of the pump housing,
wherein the second attachment portion is fitted into a second attachment target portion which is a groove formed in an upper side wall of the pump housing and extending in the front-to-back direction by turning about the first attachment portion,
wherein the second attachment portion comprises a rim extending in the front-to-back direction, which is inserted into the second attachment target portion, wherein a front end of the first attachment portion is positioned on a rotor side with respect to a front end of the second attachment portion when the tube holder is attached to the pump housing, and wherein the extracorporeal circuit has a storage form in which the pump tube is bundled with line tubes other than the pump tube using bundling portions which are attached such as at least part thereof is positioned on both sides of a loop top position of the loop of the pump tube.

9. The extracorporeal circuit of claim 8, wherein the second tube holding portion functions as a sensor driver that drives a tube holder attachment sensor provided at the housing when the second attachment portion is attached to the second attachment target portion.

10. The extracorporeal circuit of claim 8, wherein the pump tube is held in a twisted state between the first tube holding portion and the second tube holding portion.

11. An extracorporeal circuit assembled with a dialysis machine having a pump portion on a side surface of a housing, the pump portion having a rotor and a pump housing, the extracorporeal circuit comprising:

a pump tube assembled with the rotor of the pump portion;

a line tube; and a tube holder holding the pump tube and the line tube and detachably attached to the pump housing, wherein the tube holder has first and second tube holding portions holding the pump tube in a loop shape and holding the line tube and a fixing plate coupling the first tube holding portion and the second tube holding portion to each other, and wherein the fixing plate has a raised portion protruding from a center portion in a thickness direction, the raised portion being pushed by a pushing pin formed on the pump portion such that the tube holder is released from the pump housing.

* * * * *